(12) United States Patent
Ugwu et al.

(10) Patent No.: US 12,377,045 B2
(45) Date of Patent: Aug. 5, 2025

(54) ORAL LIQUID FORMULATIONS OF LIPID-LOWERING AND BLOOD PRESSURE-LOWERING DRUGS

(71) Applicant: FORDOZ PHARMA CORP., East Windsor, NJ (US)

(72) Inventors: Sydney Ugwu, North Brunswick, NJ (US); Zengli Fu, Kendall Park, NJ (US); James He, Green Brook, NJ (US)

(73) Assignee: FORDOZ PHARMA CORP., East Windsor, NJ (US)

( * ) Notice: Subject to any disclaimer, the term of this patent is extended or adjusted under 35 U.S.C. 154(b) by 239 days.

(21) Appl. No.: 17/768,049

(22) PCT Filed: Nov. 24, 2020

(86) PCT No.: PCT/US2020/061911
§ 371 (c)(1),
(2) Date: Apr. 11, 2022

(87) PCT Pub. No.: WO2021/108343
PCT Pub. Date: Jun. 3, 2021

(65) Prior Publication Data
US 2024/0091147 A1    Mar. 21, 2024

Related U.S. Application Data

(60) Provisional application No. 62/939,729, filed on Nov. 25, 2019.

(51) Int. Cl.
| | | |
|---|---|---|
| *A61K 9/08* | (2006.01) | |
| *A61K 31/216* | (2006.01) | |
| *A61K 31/366* | (2006.01) | |
| *A61K 31/397* | (2006.01) | |
| *A61K 31/40* | (2006.01) | |
| *A61K 31/4422* | (2006.01) | |
| *A61K 47/12* | (2006.01) | |
| *A61K 47/14* | (2017.01) | |
| *A61K 47/26* | (2006.01) | |
| *A61K 47/44* | (2017.01) | |

(52) U.S. Cl.
CPC .............. *A61K 9/08* (2013.01); *A61K 31/216* (2013.01); *A61K 31/366* (2013.01); *A61K 31/397* (2013.01); *A61K 31/40* (2013.01); *A61K 31/4422* (2013.01); *A61K 47/12* (2013.01); *A61K 47/14* (2013.01); *A61K 47/26* (2013.01); *A61K 47/44* (2013.01)

(58) Field of Classification Search
CPC ...... A61K 9/08; A61K 31/216; A61K 31/366; A61K 31/397; A61K 31/40; A61K 31/4422; A61K 47/12; A61K 47/14; A61K 47/26; A61K 47/44; A61K 9/0095; A61K 9/0053; A61K 47/10; A61K 2300/00; A61P 3/06; A61P 9/10; A61P 9/12
See application file for complete search history.

(56) References Cited

U.S. PATENT DOCUMENTS

| 2010/0061968 | A1 | 3/2010 | Lines |
| 2019/0269713 | A1* | 9/2019 | Gordts ..................... A61K 9/20 |

FOREIGN PATENT DOCUMENTS

| CN | 102349909 | 2/2012 |
| JP | 2009256216 | 11/2009 |
| WO | 199911263 | 3/1999 |
| WO | 2010098906 | 9/2010 |

OTHER PUBLICATIONS

PCT International Search Report for PCT/US2020/061911, Mar. 11, 2021.
PCT International Written Opinion for PCT/US2020/061911, Mar. 11, 2021.

* cited by examiner

*Primary Examiner* — Robert A Wax
*Assistant Examiner* — Quanglong N Truong
(74) *Attorney, Agent, or Firm* — FLOREK & ENDRES PLLC

(57) ABSTRACT

This application discloses oral liquid formulations of lipid/cholesterol-lowering drugs and blood pressure-lowering drugs, and combinations thereof, comprising surfactant(s) as stabilizer(s), which forms micelles with the drug molecules to enhance their solubility and stability.

22 Claims, No Drawings

ORAL LIQUID FORMULATIONS OF LIPID-LOWERING AND BLOOD PRESSURE-LOWERING DRUGS

This application is the U.S. National Stage filing of International Patent Application Number PCT/US2020/061911, filed on Nov. 24, 2020 which claims the benefits of U.S. Provisional Patent Application Ser. No. 62/939,729 filed Nov. 25, 2019, the contents of which are incorporated herein by reference.

FIELD OF THE INVENTION

The present disclosure relates to oral liquid formulations for the treatment and prevention of hyperlipidemia, mixed dyslipidemia, heterozygous familial hypercholesterolemia, artherosclerotic cardiovascular disease, hypertension, and/or coronary artery disease.

BACKGROUND OF THE INVENTION

Lipid-lowering drugs are used to a) reduce the risk of coronary heart disease mortality and deaths, b) reduce the risk of non-fatal myocardial infarction and stroke and c) reduce the need for coronary artery revascularization procedures. Lipid-lowering drugs are also indicated as an adjunct to diet for treatment of hyperlipidemia, including reduction in elevated total cholesterol and triglycerides and elevation in high density lipoprotein. These class of drugs are useful for treatment of adolescent patients with heterozygous familial hypercholesterolemia.

Several lipid-lowering drugs are commercially available. These include: 1) HMG-CoA inhibitors (statins) such as simvastatin, lovastatin, pravastatin, fluvastatin, mevastatin, atorvastatin, rosuvastatin, pitavastatin and pharmaceutically acceptable salts thereof; 2) cholesterol absorption inhibitors such as ezetimibe; 3) bile acid sequestrants such as cholestyramine, colestipol and colesevelam; 4) nicotinic acid (aka niacin), esters of nicotinic acid and pharmaceutically acceptable salts thereof; 5) fibrates such as bezafibrate, ciprofibrate, clinofibrate, clofibrate, clofibride, fenofibrate, gemfibrozil, ronifibrate, simfibrate and pharmaceutically acceptable salts thereof; 6) PCSK9 inhibitors such as alirocumab, bococizumab and evolocumab. These lipid-lowering drugs can be used alone or in combination with other lipid lowering drugs or blood pressure-lowering drugs to treat hyperlipidemia, hypertension and coronary artery disease. Examples of commercially available combination drug products include: simvastatin/ezetimibe and atorvastatin and amlodipine (antihypertensive drug). Most of the lipid-lowering drugs possess low solubility and low stability in aqueous solutions which make them difficult to formulate in aqueous solution.

The commercially available blood pressure-lowering drugs may be classified into the following categories: angiotension-converting-enzyme inhibitors ("ACE inhibitors"), calcium channel blockers ("CCBs"), angiotensin receptor blockers ("ARBs"), alpha-adrenergic blockers, central sympatomimetics, diuretics, and vasodilators. Examples of ACE inhibitors include alacepril, benzapril, captopril, cilazapril, enalapril, fosinopril, imidapril, lisinopril, perindopril, quinapril, ramipril, trandolapril, zefnopril and pharmaceutically acceptable salts thereof. Examples of CCBs include amlodipine, aranidipine, azelnidipine, barnidipine, benidipine, clinidipine, diltiazem, efonidipine, felodipine, fendiline, gallopamil, isradipine, lacidipine, lercanidipine, mandipine, nicardipine, nifedipine, nilvadipine, nimodipine, nisoldipine, nitrendipine, prandipine, verapamil, and pharmaceutically acceptable salts thereof. Examples of ARBs include, azilstartan, candesartan, eprosartan, fimasartan, irbesartan, losartan, olmesartan, telmisartan, valsartan and pharmaceutically acceptable salts thereof. Examples of alpha-adrenergic blockers include doxazosin, prazosin, terazosin and pharmaceutically acceptable salts thereof.

Many of the lipid-lowering and blood pressure-lowering drugs possess some significant formulation and administration issues such as low solubility and low stability. Although the lipid-lowering and blood pressure-lowering drugs represent an important class of compounds for treatment of numerous human diseases, most are only commercially available as solid-dosage forms such as tablets and capsules. Due to the importance of the lipid-lowering and blood pressure-lowering drugs, there is a need for oral liquid formulations for special patient populations, especially geriatrics, pediatrics, and/or bedridden patients who are unable to swallow oral solid dosage forms.

Thus, it is the objective of this invention to overcome the low water solubility and instability challenges of lipid-lowering and blood pressure-lowering drugs and develop oral liquid formulations, which are soluble at therapeutic concentrations and stable throughout the shelf life of the product, preferably without the need for refrigeration.

SUMMARY OF THE INVENTION

The present invention provides stable oral liquid formulations of lipid-lowering and/or blood pressure-lowering drugs that are suitable for oral administration to humans and animals. The present invention is particularly useful for lipid-lowering and blood pressure-lowering drugs that slightly soluble, very slightly soluble, practically insoluble or insoluble in water as defined by the United States Pharmacopeia. The present invention is also particularly useful for lipid-lowering and blood pressure-lowering drugs that unstable in water.

It has now been discovered that stable and therapeutically effective oral liquid formulations containing lipid-lowering and blood pressure-lowering drugs that are slightly soluble, very slightly soluble, practically insoluble or insoluble in water may be obtained by dissolving the lipid-lowering and/or blood pressure-lowering drug in one or more non-aqueous solubilizing excipients and mixing the drug/non-aqueous solubilizing excipient solution with water. In certain embodiments, the non-aqueous solubilizing excipient comprises one or more surfactants, preferably one or more surfactants with fatty acid chains and more preferably one or more nonionic surfactants. The oral liquid formulations of the present invention may further comprise pharmaceutically acceptable excipients such as antioxidants, preservatives and/or antimoicrobials, buffering/pH adjusting agents, sweetening/flavoring agents, viscosity enhancing agents, hydrophilic stabilizing agents and combinations thereof.

Another aspect of the present invention is directed to oral liquid formulations with an improved pharmacokinetic profile as compared to the counterpart solid oral dosage forms such as tablets and capsules. The improved pharmacokinetic profile includes but is not limited to an increased absorption, i.e. higher AUC values compared to a similar solid oral dosage from containing the same amount of the lipid-lowering and/or blood pressure-lowering drug. It is believed that the drug/non-aqueous solubilizing excipient solution will enhance the absorption of the lipid-lowering and blood pressure-lowering drugs that are slightly soluble, very slightly soluble, practically insoluble or insoluble in water by increasing the rate of absorption and/or by increasing the amount of absorption of the drug from a patient's or subject's gastrointestinal tract. This enhance absorption will allow for lower dosing of the drug while obtaining similar therapeutic or plasma levels as conventional solid dosage forms contain larger amounts of the drug.

Another aspect of the present invention is directed to a method of making an oral liquid formulation as described herein by (a) dissolving the lipid-lowering and/or blood pressure-lowering drugs in one or more non-aqueous solubilizing excipients and (b) mixing the drug/non-aqueous solubilizing excipient solution with water. In certain embodiments, the water of step (b) is a buffered aqueous solution. In another embodiment, the water of step (b) comprises one or more hydrophilic stabilizing agents, sweetening/flavoring agents, preservative/antimicrobial agents, viscosity enhancing agents, buffering/pH adjusting agents or combinations thereof. In a still further embodiment, the water of step (b) is a buffered aqueous solution and comprises one or more additional hydrophilic stabilizing agents, sweetening/flavoring agents, preservative/antimicrobial agents, viscosity enhancing agents, buffering/pH adjusting agents or combinations thereof. In yet a further embodiment, the drug/non-aqueous solubilizing excipient solution of step (a) may comprises one or more additional pharmaceutically acceptable excipients such co-solvents, sweetening/flavoring agents, preservative/antimicrobial agents, viscosity enhancing agents or combinations thereof. The drug/non-aqueous solubilizing excipient solution of step (a) should be free or substantially free of water prior to mixing with aqueous solution of step (b). As used herein substantially free of water means, less than 5% w/w, less than 4% w/w, less than 3% w/w, less than 2% w/w, less than 1% w/w or 0% water.

Another aspect of the present invention involves the dissolution of a lipid-lowering and/or blood pressure-lowering drug in the non-aqueous solubilizing excipients, without addition of water, to form non-aqueous compositions. Before, after or concurrently with the dissolution, other non-aqueous excipients such as co-solvents, antioxidants, preservative/antimicrobial agents, buffering/pH adjusting agents, sweetening/flavoring agents, viscosity enhancing agents and combinations thereof may be added to form a solution or suspension that is free or substantially free of water and wherein the lipid-lowering and/or blood pressure-lowering drug is dissolved or substantially dissolved, i.e., less than 5%, less than 4%, less than 3%, less than 2%, less than 1% of the total amount is drug is undissolved. These non-aqueous compositions may be taken directly as an oral solution or encapsulated in soft gel capsules and taken orally. Upon contact with water in the gastrointestinal tract, these non-aqueous compositions spontaneously form microemulsion which facilitates oral absorption.

A further aspect of the invention is directed to a method of treating hyperlipidemia, mixed dyslipidemia, or heterozygous familial hypercholesterolemia in a patient, in particular pediatric patients, or reducing cardiovascular mortality and morbidity in patients with manifest artherosclerotic cardiovascular disease, hypertension, and/or coronary artery disease, the methods comprising administering to a subject in need thereof a therapeutically effective amount of an oral liquid formulations according to any embodiment of this invention disclosed herein.

DETAILED DESCRIPTION OF CERTAIN EMBODIMENTS

Before the present invention is further described, it is to be understood that this invention is not limited to the particular embodiments described. It is also to be understood that the terminology used herein is for the purpose of describing particular embodiments only, and is not intended to be limiting.

It should be noted that as used herein, the singular forms "a," "an," and "the" include plural referents unless the context clearly dictates otherwise.

A number of ranges of values are provided in this disclosure. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention. The term "about" generally refers to plus or minus 10% of the indicated number. For example, "about 10%" may indicate a range of 9% to 11%, and "about 20" may mean from 18 to 22. Other meanings of "about" may be apparent from the context, such as rounding off, so, for example "about 1" may also mean from 0.5 to 1.4. Similarly, "about 0.2" may encompass the value 0.22.

The term "% w/w", as used herein, represents weight percentage of the component in the total weight of a liquid formulation, or a pertinent composition referred to or implied based on the context, which should be clear to a person of ordinary skill in the art.

The term "HLB" refers to the "hydrophilic-lipophilic balance" of a surfactant or emulsifier and is a measure of the degree to which it is hydrophilic or lipophilic and is determined by calculating values for the different regions of the molecule, as described by Griffin WC, "Calculation of HLB Values of Non-Ionic Surfactants," Journal of the Society of Cosmetic Chemists, 5:259 (1954). HLB values range from 0 to 20, with an HLB value of 0 corresponding to a completely lipophilic molecule, and a value of 20 corresponding to a completely hydrophilic molecule. HLB values are generally known and reported in the literature such as the manufacturer's technical brochures.

The terms "slightly soluble", "very slightly soluble," "practically insoluble," and "insoluble" should be accorded the meaning provided by the United States Pharmacopeia ("USP"). More specifically the USP provides the following table to describe solubility:

| Descriptive Term | Parts of Solvent Required for 1 Part of Solute |
|---|---|
| Very soluble | Less than 1 |
| Freely soluble | From 1 to 10 |
| Soluble | From 10 to 30 |
| Sparingly Soluble | From 30 to 100 |
| Slightly soluble | From 100 to 1000 |
| Very slightly soluble | From 1000 to 10,000 |
| Practically insoluble or insoluble | Greater than or equal to 10,000 |

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The oral liquid formulations of the present invention will comprise one or more lipid-lowering and/or blood pressure-lowering drugs, that are slightly soluble, very slightly soluble, or practically insoluble in water. Examples of the lipid-lowering and/or blood pressure-lowering drugs that are slightly soluble, very slightly soluble, or practically insoluble in water that can be used in the present invention include ezetimibe, statins such as simvastatin, lovastatin, pravastatin, fluvastatin, mevastatin, atorvastatin, rosuvastatin, pitavastatin and pharmaceutically acceptable salts thereof; bile acid sequestrants such as cholestyramine, colestipol and colesevelam; fibrates such as bezafibrate, ciprofibrate, clinofibrate, clofibrate, clofibride, fenofibrate, gemfibrozil, ronifibrate, simfibrate and pharmaceutically acceptable salts thereof; PCSK9 inhibitors such as alirocumab, bococizumab and evolocumab; ACE inhibitors such as alacepril, benzapril, captopril, cilazapril, enalapril, fosinopril, imidapril, lisinopril, perindopril, quinapril, ramipril, trandolapril, zefnopril and pharmaceutically acceptable salts thereof; CCBs such as amlodipine, aranidipine, azelnidipine, barnidipine, benidipine, clinidipine, diltiazem, efonidipine, felodipine, fendiline, gallopamil, isradipine, lacidipine, lercanidipine, mandipine, nicardipine, nifedipine, nilvadipine, nimodipine, nisoldipine, nitrendipine, prandipine, verapamil, and pharmaceutically acceptable salts thereof; ARBs such as azilstartan, candesartan, eprosartan, fimasartan, irbesartan, losartan, olmesartan, telmisartan, valsartan and pharmaceutically acceptable salts thereof and alpha-adreneergic blockers such as doxazosin, prazosin, and terazosin.

In certain preferred embodiments, oral liquid formulations of the present invention will comprise one or more lipid-lowering and/or blood pressure-lowering drug, that is slightly soluble, preferably very slightly soluble, and most preferably practically insoluble or insoluble in water selected ezetimibe, statins such as simvastatin, lovastatin, atorvastatin (including alkali metal and alkali earth metal salts such a sodium, potassium calcium and magnesium salts), rosuvastatin (including alkali metal and alkali earth metal salts such a sodium, potassium calcium and magnesium salts), fibrates such as clofibrate, fenofibrate, choline fenofibrate, gemfibrozil, ACE inhibitors such as benzapril, captopril, enalapril, fosinopril, quinapril, ramipril, and pharmaceutically acceptable salts thereof; CCBs such as amlodipine (including the besylate, benzoate, maleate and mesylate salts), felodipine, isradipine, nicardipine, nifedipine, nisoldipine and pharmaceutically acceptable salts thereof; ARBs such candesartan, candesartan cilexetil, irbesartan, losartan, olmesartan, telmisartan, valsartan and pharmaceutically acceptable salts and combinations thereof.

In certain embodiments the oral liquid formulations of the present invention will comprise:
(a) 0.05%-10% w/w, preferably 0.1%-5% w/w and most preferably 0.15-2.5% w/w of ezetimibe;
(b) 0.05%-20% w/w, preferably 0.1%-10% w/w and most preferably 0.15-5 wt % of a statin or salt thereof;
(c) 0.05%-10% w/w, preferably 0.1%-5% w/w, most preferably 0.15-2.5% w/w fenofibrate;
(d) 0.05%-20% w/w, preferably 0.1%-10% w/w, most preferably 0.15%-5% w/w of an ACE inhibitor, a CCB, and/or an ARB, preferably the ACE inhibitor, CCB and/or ARB is benzapril, captopril, enalapril, fosinopril, quinapril, ramipril, amlodipine (including the besylate, benzoate, maleate and mesylate salts), felodipine, isradipine, nicardipine, nifedipine, nisoldipine, candesartan, candesartan cilexetil, irbesartan, losartan, olmesartan, telmisartan, valsartan pharmaceutically acceptable salts thereof or combinations thereof;
(e) 0.05%-10% w/w, preferably 0.1%-5% w/w and most preferably 0.15-2.5% w/w of ezetimibe in combination with 0.05%-20%, preferably 0.1%-10% w/w and most preferably 0.15%-5 wt % of a statin or salt thereof;
(f) 0.05%-10% w/w, preferably 0.1%-5% w/w and most preferably 0.15-2.5% w/w of ezetimibe in combination with 0.05%-10% w/w, preferably 0.1%-5% w/w and most preferably 0.15%-2.5% w/w fenofibrate;
(g) 0.05%-10% w/w, preferably 0.1%-5% w/w and most preferably 0.15-2.5% w/w of ezetimibe in combination with 0.05%-20% w/w, preferably 0.1%-10% w/w, most preferably 0.15%-5% w/w of an ACE inhibitor, a CCB, and/or an ARB, preferably the ACE inhibitor, CCB and/or ARB is benzapril, captopril, enalapril, fosinopril, quinapril, ramipril, amlodipine (including the besylate, benzoate, maleate and mesylate salts), felodipine, isradipine, nicardipine, nifedipine, nisoldipine, candesartan, candesartan cilexetil, irbesartan, losartan, olmesartan, telmisartan, valsartan pharmaceutically acceptable salts thereof or combinations thereof;
(h) 0.05%-20% w/w, preferably 0.1%-10% w/w and most preferably 0.15%-5 wt % of a statin or salt thereof in combination with 0.05%-20% w/w, preferably 0.1%-5% w/w, most preferably 0.15%-2.5% w/w fenofibrate;
(i) 0.05%-20% w/w, preferably 0.1%-10% w/w and most preferably 0.15%-5 wt % of a statin or salt thereof in combination with 0.05%-20% w/w preferably 0.1%-10% w/w, most preferably 0.15%-5% w/w of an ACE inhibitor, a CCB, and/or an ARB, preferably the ACE inhibitor, CCB and/or ARB is benzapril, captopril, enalapril, fosinopril, quinapril, ramipril, amlodipine (including the besylate, benzoate, maleate and mesylate salts), felodipine, isradipine, nicardipine, nifedipine, nisoldipine, candesartan, candesartan cilexetil, irbesartan, losartan, olmesartan, telmisartan, valsartan pharmaceutically acceptable salts thereof or combinations thereof; or
(i) 0.05%-20% w/w, preferably 0.1%-5% w/w, most preferably 0.15%-2.5% w/w fenofibrate in combination with 0.05%-20% w/w, preferably 0.1%-10% w/w, most preferably 0.15%-5% w/w of an ACE inhibitor, a CCB, and/or an ARB, preferably the ACE inhibitor, CCB and/or ARB is benzapril, captopril, enalapril, fosinopril, quinapril, ramipril, amlodipine (including the besylate, benzoate, maleate and mesylate salts), felodipine, isradipine, nicardipine, nifedipine, nisoldipine, candesartan, candesartan cilexetil, irbesartan, losartan, olmesartan, telmisartan, valsartan pharmaceutically acceptable salts thereof or combinations thereof.

The oral liquid formulations of the present invention may also comprise one or more drugs including but not limited to lipid-lowering and blood pressure-lowering drugs that are very soluble, freely soluble, soluble and/or sparing soluble in water, provided the oral liquid formulations comprise one or more lipid-lowering and/or blood pressure-lowering drug, that is slightly soluble, very slightly soluble, or practically insoluble in water.

The non-aqueous solubilizing excipients of the present invention should be a liquid at ambient conditions, i.e., 25°

C. and standard atmospheric pressure and should be capable of dissolving the lipid-lowering and/or blood pressure-lowering drug that is slightly soluble to insoluble in water. The non-aqueous solubilizing excipients should comprise about 10%-90% w/w of the oral liquid composition, preferably about 10%-80% w/w and most preferably 10%-75% w/w of the oral liquid composition. In certain embodiments, the non-aqueous solubilizing excipient should comprise at least about 10%, 15%, 20%, 25%, 30, 35%, 40% or 50% w/w of the oral liquid composition and less than 90%, 85%, 80%, 75%, 70%, 65%, 60%, 55% or 50% w/w of the oral liquid composition. The non-aqueous solubilizing excipient may be a surfactant, preferably a surfactant comprising a fatty acid moiety, preferably a C8 to C20 fatty acid moiety. The non-aqueous solubilizing excipient may also be an ionic or non-ionic surfactant.

Examples of non-ionic surfactants that may be used include polyethoxylated castor oil, a polyoxyethylene alkyl ester, a polyglycolyzed glyceride, a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, a polyoxyethylene fatty acid ester, a polyoxyethylene sorbitan fatty acid ester, a polyoxyethylene glycerin fatty acid ester, a polyoxyethylene hydrogenated castor oil, a polyoxypropylene fatty acid ester, polyoxylglycerides, polyoxyethylene stearates or a mixture of the foregoing. A further listing of possible non-ionic surfactants can be found on pages 1243-1249 of Martindale, The Extra Pharmacopoeia, 29th ed. which is incorporated herein by reference.

In certain embodiments, the non-aqueous solubilizing excipient comprises one or more surfactants, preferably a non-ionic surfactant that exhibits an HLB value of 10 or greater, about 11 or greater, about 12 or greater, about 13 or greater or about 14 or greater.

In certain embodiments the non-aqueous solubilizing excipient comprises one or more surfactants, preferably a non-ionic surfactant that exhibits an HLB value of less than 10, more preferably an HLB value of about 9 or less, about 8 or less, about 7 or less, about 6 or less, or about 5 or less.

In certain embodiments the non-aqueous solubilizing excipient comprises a mixture of (i) one or more surfactants, preferably a non-ionic surfactant, that exhibits an HLB value of 10 or greater, about 11 or greater, about 12 or greater, about 13 or greater or about 14 or greater and (ii) one or more surfactants, preferably a non-ionic surfactant, that exhibits an HLB value of less than 10, more preferably an HLB value of about 9 or less, about 8 or less, about 7 or less, about 6 or less, or about 5 or less. The weight ratio of the one or more surfactants with an HLB value of 10 or greater to the one or more surfactants with an HLB value of less than 10 may range from 0.2:1 to 1:02, preferably 0.5:1 to 1:05 and most preferably 0.75:1 to 1:0.75.

In another embodiment of the present invention, the oral liquid formulations will comprise one or more surfactants that exhibits an HLB value of 10 or greater, about 11 or greater, about 12 or greater, about 13 or greater or about 14 or greater in an amount of 10% w/w or greater based on the total weight of the oral liquid formulation, preferably in an amount of about 15% w/w or greater and most preferably in an amount of about 20% w/w or greater based on the total weight of the composition. In certain embodiments, the one or more surfactants that exhibit an HLB value of 10 or greater may be present in the composition in an amount of about 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48% 49% 50%, 51%, 52%, 53%, 54%, 55%, 56%, 57%, 58%, 59%, 60% w/w or any range encompassed by the foregoing values.

Examples of the one or more surfactants that exhibits an HLB value of 10 or greater may be a non-ionic surfactant such as fatty alcohol acid or amide ethoxylates, monoglyceride ethoxylates, sorbitan ester ethoxylates alkyl polyglycosides, and mixtures thereof. Examples of these non-ionic surfactants include but are not limited to polyoxyethylene derivatives of polyol esters, such as Polysorbate 20 (commercially available under the tradename TWEEN® 20), Polysorbate 40 (commercially available under the tradename TWEEN® 40) Polysorbate 60 (commercially available under the tradename TWEEN® 60), and Polysorbate 80 (commercially available under the tradename TWEEN® 80).

Examples of the one or more surfactants that exhibit an HLB value of 10 or greater also include polyoxyethylene castor oils such as polyoxyl castor oil or polyoxyl hydrogenated castor oil or mixtures thereof. Examples of these surfactants include but are not limited to polyoxyl 35 castor oil (commercially available under the tradename CREMAPHOR EL or KOLLIPHOR EL), polyoxyl 40 hydrogenated castor oil (commercially available under the tradename CREMOPHOR RH 40) and polyoxyl 60 hydrogenated castor oil.

Further examples of the one or more surfactants that exhibits an HLB value of about 10 or greater include a polyoxyethylene alkyl ether such as a polyoxyl cetostearyl ether, polyoxyl cetyl ether, polyoxyl lauryl ether, polyoxyl oleyl ether, polyoxyl stearyl ether a tyloxapol, a poloxamer, i.e., a non-ionic polyoxyethylene-polyoxypropylene copolymers such as poloxamer 188, poloxamer 237, poloxamer 338, poloxamer 407, a fatty acid ester or fatty acid alcohol of a polyglyceride such as a caprylic/capric triglyceride (commercially available under the tradename MYIGLYOL) or combinations thereof.

In certain embodiments of the present invention, the oral liquid dosage forms may comprise one or more surfactants that exhibit an HLB value of about less than 10, more preferably an HLB value of about 9 or less, about 8 or less, and most preferably an HLB value of about 7 or less. Examples of the one or more surfactants with an HLB value less than 10 include but are not limited to polyethoxylated castor oil, a polyoxyethylene alkyl ester, a polyglycolyzed glyceride, a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, a polyoxyethylene fatty acid ester, a polyoxyethylene sorbitan fatty acid ester, a polyoxyethylene glycerin fatty acid ester, a polyoxyethylene hydrogenated castor oil, a polyoxypropylene fatty acid ester, or a mixture of the foregoing. A further listing of possible non-ionic surfactants with low HLB values can be found on pages 1243-1249 of Martindale, The Extra Pharmacopoeia, 29th ed. which is incorporated herein by reference.

In certain embodiments, the one or more surfactants with an HLB value less than can comprise is a medium chain (i.e., about 4 to about 20 carbon atoms, preferably about 6 to about 18 carbon atoms and most preferably about 6 to and 14 carbon atoms) monoglyceride or diglyceride such as a glyceryl caprylate/caprate (commercially available under the tradename CAPMUL MCM), a glyceryl caprylate (commercially available under the tradename CAPMUL MCM C8), glyceryl caprate (commercially available under the tradename CAPMUL MCM C10), glyceryl monocaprylocaprate (commercially available under the tradename CAPMUL 471) or mixtures thereof.

In certain embodiments, the one or more surfactants with an HLB value less than 10 may comprise a polyoxylglyceride such as caprylocaproyl polyoxylglycerides (LABRASOL®), lauroyl polyoxylglycerides, linoleoyl polyoxylglycerides, oleoyl polyoxylglycerides, stearoyl polyoxylglycerides, and mixtures of the foregoing.

In certain embodiments, the one or more surfactants with an HLB value less than 10 is a sorbitan ester or sorbitan fatty acid ester such as sorbitan monolaurate, sorbitan monooleate, sorbitan monopalmitate, sorbitan monostearate, sorbitan sesquioleate, sorbitan trioleate, tyloxapol, and mixtures of the foregoing.

In certain embodiments, the one or more surfactants with an HLB value less than is a phospholipid or lecithin.

In the embodiments the amount of the one or more surfactants with an HLB value about less than 10 may be present in the oral liquid dosage formulations in an amount of 10% w/w or greater based on the total weight of the oral liquid formulations, preferably in an amount of about 15% w/w or greater and most preferably in an amount of about 20 wt % or greater based on the total weight of the oral liquid formulations. In certain embodiments, the one or more surfactants that exhibit an HLB value of about 10 or greater may be present in the composition in an amount of about 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 0.43%, 44%, 45%, 46%, 47%, 48%, 49%, 50%, 51%, 52%, 53%, 54%, 55%, 56%, 57%, 58%, 59%, 60% w/w or greater or any range encompassed by the foregoing values.

In certain embodiments, the non-aqueous solubilizing excipient may further comprise a co-solvent. Examples of co-solvents include an oil, such as corn oil, sesame oil, cotton seed oil, peanut oil etc, low molecular weight polyols such as glycerin, propylene glycol, polyethylene glycols (PEG) that are a liquid at ambient conditions such as PEG 200, PEG 300, PEG 400 and PEG 600, C1-C6 straight and branch monoalcohols such ethanol and benzoyl alcohol. If a co-solvent is present, it should comprise about 0.05%-10% w/w, preferably about 0.1%-7.5% w/w and most preferably about 0.5%-5% w/w of the oral liquid formulations.

The oral liquid formulations of the present invention may further comprise one or more known pharmaceutically acceptable excipients such as antioxidants, preservatives and/or antimoicrobials, buffering/pH adjusting agents, sweetening/flavoring agents, viscosity enhancing agents, hydrophilic stabilizing agents and combinations thereof.

Examples of antioxidants that may be used in the present invention include, but are not limited to, ascorbic acid, ascorbyl palmitate (AP), butylated hydroxyanisole (BHA), butylated hydroxytoluene (BHT), citric acid, ethyl oleate, fumaric acid, hypophosphorous acid, malic acid, monothioglycerol, potassium metabisulfite, propyl gallate, sodium bisulfite, sodium formaldehyde sulfoxylate, sodium metabisulfite, sodium sulfite, sodium thiosulfate, sulfur dioxide, tocopherols, methylparaben, ethylparaben, propylparaben, butylparaben, benzyl benzoate, pyridoxine, ethyl vanillin and mixtures thereof. Preferred antioxidants for use according to the invention include BHT, BHA, AP, propyl gallate, alpha tocopherol, or any mixtures thereof. Generally, the amount antioxidant present in the composition of the present invention will comprise about 0.0001% w/w to about 5% w/w, preferably about 0.001% w/w to about 2% w/w, and most preferably about 0.01% w/w to about 1% w/w based on the total weight of the composition.

Examples of buffers or buffering agents that may be used in the present invention include, but are not limited to, acetic acid, adipic acid, ammonium carbonate, ammonium phosphate, boric acid, citric acid, lactic acid, phosphoric acid, potassium citrate, potassium phosphate, sodium acetate, sodium citrate, sodium carbonate, potassium carbonate, sodium bicarbonate, potassium bicarbonate, sodium lactate, sodium phosphate, succinic acid, and combinations thereof. Typically the buffer will comprise a combination of the foregoing as to create a buffer system such as citric acid and sodium citrate or acetic acid and sodium acetate.

Examples of pH adjusting agents that may be used in the present invention include, but are not limited to, any of the pharmaceutically acceptable acids or bases used to adjust the pH of pharmaceutical compositions. Examples of compounds typically used to adjust the pH of pharmaceutical compositions include hydrochloric acid, citric acid, lactic acid, tartaric acid, glacial acetic acid, sodium hydroxide, potassium hydroxide, arginine, lysine, meglumine, triethanol amine, or combinations thereof.

If employed, the buffer/pH adjusting agent may comprise about 0.01% w/w to about 20% w/w of the composition, preferably about 0.05% w/w to about 10% w/w of the composition, and most preferably about 0.1% w/w to about 5% w/w of the composition. In certain embodiments, the amount of buffering/pH adjusting agents present in the oral liquid formulation should be present in an amount sufficient to produce and maintain during storage a pH of the oral liquid formulation of about 3-8, preferably about 4-7 and most preferably about 4-5, 5-6 or 6-7. The oral liquid dosage form should maintain the pH for at least six months, 9 months, 12 months, 18 months, or 24 months under normal storage conditions.

Hydrophilic stabilizing agents as used herein includes hydrophilic excipients capable of forming hydrogen-bonds with water molecules to decrease water activity, which in turn stabilizes the lipid-lowering and/or blood pressure-lowering drugs against hydrolysis. Examples of suitable hydrophilic stabilizing agents include, but are not limited to, sorbitol, sucrose, lactose, starch, dextrose, sucrose, fructose, maltose, mannitol, xylitol and combinations thereof. If employed the hydrophilic stabilizing agent should be present in the oral liquid formulations in an amount of about 0.01%-30% w/w, preferably 0.05%-20% w/w and most preferably contain 0.1%-10% w/w.

Viscosity enhancing agents that may be used in the present invention include organic materials such as natural or synthetic waxes, C12-C60 alcohols, C12-C60 acids, alpha-hydroxy fatty acids, polyhydroxy fatty acid esters, polyhydroxy fatty acid amides, and inorganic/organic materials such as metal ester complexes containing zinc, calcium, aluminum or magnesium, fumed silicas, and organoclays. Additional viscosity enhancing agents include polyol polyesters, glyceryl esters, polyglyceryl esters, and polysiloxanes.

Waxes are also suitable for use as viscosity enhancing agents in compositions of the present invention. Natural waxes may include, but are not limited to, carnauba, ozokerite, beeswax, candelilla, paraffin, ceresin, esparto, ouricuri, rezowax and other known mined and mineral waxes. Synthetic waxes may include, but are not limited to, paraffin waxes and microcrystalline waxes.

Still further viscosity enhancing agents that may be included in the compositions of the present invention are gelling agents. Gelling agents are materials that can swell or expand when in contact with water. Examples of gelling agents that may be used in the present invention include swellable polymers, also known as osmopolymers or hydrogels. The swellable polymer can be non-cross-linked or lightly cross-linked. The cross-links can be covalent or ionic bonds with the polymer possessing the ability to swell in the presence of fluid, and when cross-linked, it will not be dissolved in the fluid. The polymer can be of plant, animal, or synthetic origin. Polymeric gelling agents useful for the present purpose include polyhydroxyalkylcellulose having a molecular weight greater than 50,000, such as hydroxyl propylmethylcellulose (METHOCEL K 100M available from Dow Chemical); poly(hydroxyalkylmethacrylate) having a molecular weight of from 5,000 to 5,000,000; poly (vinylpyrrolidone) having a molecular weight of from 100,000 to 3,000,000; anionic and cationic hydrogels; poly (electrolyte) complexes; poly(vinylalcohol) having a low acetate residual; a swellable mixture of agar and carboxymethyl cellulose; a swellable composition comprising methyl cellulose mixed with a sparingly cross-linked agar; a polyether having a molecular weight of from 10,000 to 6,000,000; a water-swellable copolymer produced by a dispersion of a finely divided copolymer of maleic anhydride with styrene, ethylene, propylene, or isobutylene; a water-swellable polymer of N-vinyl lactams, and the like.

Other gelling agents useful in the present invention include pectin having a molecular weight ranging from 30,000 to 300,000; polysaccharides such as agar, acacia, karaya, tragacanth, algins and guar; CARBOPOL® an acrylic acid polymer, a carboxyvinyl polymer, sometimes referred to as carboxypolymethylene, a polymer of acrylic acid cross-linked with a polyallyl ether of sucrose, as described in U.S. Pat. Nos. 2,798,053 and 2,909,462 and available as CARBOPOL® 934, 940 and 941, and its salt derivatives; polyacrylamides; water-swellable indene maleic anhydride polymers; GOOD-RITE® polyacrylic acid having a molecular weight of 80,000 to 200,000; POLYOX™ polyethylene oxide polymers having a molecular weight of 100,000 to 7,000,000; starch graft copolymers; AQUA-KEEP™ acrylate polymers with water absorbability of about 400 times its original weight; diesters of polyglucan; a mixture of cross-linked polyvinyl alcohol and poly(N-vinyl-2-pyrrolidone); poly(ethylene glycol) having a molecular weight of 4,000 to 100,000. Representative polymers possessing gelling properties are described in U.S. Pat. Nos. 6,419,954, 4,915,949, 4,327,725, 4,207,893 and in Handbook of Common Polymers, by Scott and Roff, published by Cleveland Rubber Company, Cleveland, Ohio.

Other examples of viscosity enhancing agents include acacia, povidone, hypromellose, hydroxypropyl cellulose, hydroxyethyl cellulose, polyethylene oxide, polymethacrylates, methyl cellulose, ethyl cellulose, pregelatinized starch, gelatin, tragacanth, zein, or mixtures thereof. In certain embodiments, the viscosity enhancing agent is water soluble such as povidone, hypromellose, hydroxypropyl cellulose, gelatin and mixtures thereof.

Generally, the amount of viscosity enhancing agent present in the compositions of the present invention will comprise about 0% w/w to about 10% w/w, preferably about 0.01% w/w to about 5% w/w, and most preferably about 0.05% w/w to about 3% w/w based on the total weight of the composition.

Examples of sweetening/flavoring agents that may be employed in the solid dosage form of the present invention include natural and artificial sweeteners such as sucrose, aspartame, saccharin, dipotassium glycyrrhizinate, *stevia*, thaumatin and combinations thereof. Flavoring agents that may be employed include citric acid, mint, spearmint, peppermint, wintergreen, anise, walnut, almond, menthol, lemon, lime, orange, grape, cherry, raspberry, bubblegum, chocolate and vanilla extracts or oils and combinations thereof. Additional taste enhancing agents are described in U.S. Pat. No. 6,027,746, which is incorporated herein by reference. The amount of sweetening/flavoring agents present in the oral liquid formulations with vary depending upon the particular taste profile but should be present in an amount to impart an acceptable taste profile.

Examples of preservatives and/or antimicrobial agents that may be employed in the oral liquid formulations of the present invention include benzalkonium chloride, benzethonium chloride, benzoic acid, benzyl alcohol, butylparaben, cetrimonium bromide, cetylpyridinium chloride, chlorobutanol, chlorocresol, ethylparaben, methylparaben, phenol, phenoxyethanol, phenylethyl alcohol, potassium benzoate, potassium sorbate, propylparaben, sodium benzoate, sodium dehydroacetate, sodium propionate, sorbic acid, thimersol, thymol and combinations thereof. The preservative and/or antimicrobial agent or agents may be present in the oral liquid formulations of the present invention in an amount from about 0.001% w/w to about 5% w/w of the oral liquid formulation, preferably about 0.005% w/w to about 2.5% w/w of the oral liquid formulation and most preferably about 0.01% w/w to about 1.0% w/w of the oral liquid formulation.

The oral liquid formulations of the present invention are stable under standard storage conditions or accelerated conditions. The total amount of impurities in the formulations may be not more than about 0.1 to 3%, and standard storage conditions may comprise a temperature of about 20 to 25° C. (i.e., room temperature) and no more than about 40% Relative Humidity (RH). In one embodiment, the formulations disclosed herein are stable at room temperature for 18 to 24 months or longer. The stability of a formulation according to the present disclosure can be determined, for example, by measuring the physical state of the formulation, including the pH, presence of any discoloration and chemical stability by measuring assay of drug and related compounds, such as degradations products or known impurities of the drug substance.

In some embodiments, the oral liquid formulations of the present disclosure are stable when subject to predetermined conditions for predetermined times. For example, oral liquid formulations of the present disclosure can be stored at various predetermined temperatures and relative humidities for defined or predetermined time periods, for example in a closed single or multiple dose clear or amber glass bottle with a conventional child resistant screw cap and with or without a press-in bottle adapter/orifice reducer with a dip tube. In some embodiments, formulations of the disclosure are stable upon storage at Controlled Room Temperature (CRT) (25° C./60% RH), i.e. without the need for refrigeration, for up to 3 months, and it exhibited good stability whereby the drug assay value over the storage period remains at 98% or greater of the initial drug assay. The following table shows the stability values for the oral liquid formulations stored at CRT for periods of 1, 2, 3, 4, 5, 6, 7, 8, 9, 10, 11, 12 months or longer:

|  | Amount | Preferred Amount | Most Preferred Amount |
|---|---|---|---|
| Individual Known Impurity | Less than 0.5% | Less than 0.25% | Less than 0.15% |
| Total Known Impurities | Less than 1% | Less than 0.75% | Less than 0.5% |
| Individual Unknown Impurity | Less than 0.5% | Less than 0.4% | Less than 0.3% |
| Total Unknown Impurities | Less than 1% | Less than 0.75% | Less than 0.5% |
| Assay | Not less than 98% of Initial value | Not less than 98.5% of Initial value | Not less than 99% of Initial value |

The following examples of oral liquid formulations containing lipid-lowering and/or blood-pressure lowering drugs that are slightly soluble, very slightly soluble, practically insoluble or insoluble in water are illustrative in nature and are not intended to be limiting in any way.

EXAMPLES

Example 1—Preparation of Oral Solutions of Ezetimibe and Simvastatin

A preservative-antioxidant solution was prepared by dissolving 9 g methylparaben (Spectrum Chemicals), 1 g propylparaben (Spectrum Chemicals), and 1 g butylated hydroxyanisole (Sigma-Aldrich) in 100 mL propylene glycol (BioWorld) to make a stock solution. Next, 0.3 M citrate buffer was prepared by dissolving 2.24 g sodium citrate dihydrate (Sigma-Aldrich), and 1.44 g citric acid (TCI) in 50 mL purified water, and the pH was adjusted to 3.06 with 2 M HCl (Spectrum Chemicals). To prepare a 6 mL formulation, 4.331 g labrasol (Gattefosse), 128 mg preservative-antioxidant solution, 48.2 mg simvastatin (AstraTech), 12.4 mg ezetimibe (Ark Pharma), 62.5 mg anise oil flavor (LorAnn Oils), and 61.5 mg cherry oil flavor (Spectrum Chemical) were mixed together to form a pink solution (Solution I). Next, 60.1 mg sucrose (Sigma Chemicals), 60.8 mg saccharin sodium (Spectrum Chemicals), 627.6 mg stock citrate buffer solution, and 912 mg purified water were mixed together to form a clear solution (Solution II). Solution I and Solution II were mixed together to form the final clear pink liquid formulation. The final concentration of simvastatin and ezetimibe in the formulation were 8 mg/mL and 2 mg/mL, respectively.

The procedure outline din Example 1 was used to prepare Examples 2-10

Example 2

| Constituent | Amount (% w/w) | Function |
|---|---|---|
| Ezetimibe | 0.2 | API |
| Simvastatin | 0.8 | API |
| Labrasol | 69 | Stabilizer/solubilizer |
| Propylene glycol | 2.0 | Solubilizer |
| Methylparaben | 0.18 | Preservative |
| Propylparaben | 0.02 | Preservative |
| Butylated hydroxyanisole (BHA) | 0.02 | Antioxidant |
| Sodium citrate dihydrate | 0.45 | BufferIng agent |
| Citric acid | 0.29 | Buffering agent |
| Anise oil | 1.0 | Flavoring agent |
| Cherry oil | 1.0 | Flavoring agent |
| Sucrose | 1.0 | Sweetener |
| Saccharin sodium dihydrare | 1.0 | Sweetener |
| Purified water QS AD | 25 | Solvent |

Example 3

| Constituent | Amount (% w/w) | Function |
|---|---|---|
| Ezetimibe | 0.2 | API |
| Simvastatin | 1.6 | API |
| Polysorbate 20 | 42.4 | Stabilizer/solubilizer |
| Propylene glycol | 2.0 | Solubilizer |
| Methylparaben | 0.18 | Preservative |
| Propylparaben | 0.02 | Preservative |
| Butylated hydroxyanisole (BHA) | 0.02 | Antioxidant |
| Sodium citrate dihydrate | 0.45 | Bufferng agent |
| Citric acid | 0.29 | Buffering agent |
| Anise oil | 1.0 | |
| Cherry oil | 1.0 | Flavoring agent |
| Sucrose | 1.0 | Sweetner |
| Saccharin sodium dihydratre | 1.0 | |
| Purified water QS AD | 48.8 | Solvent |

Example 4

| Constituent | Amount (% w/w) | Function |
|---|---|---|
| Ezetimibe | 0.2 | API |
| Simvastatin | 1.6 | API |
| Polyoxyethylene glycol 35 castor oil | 42.4 | Stabilizer/solubilizer |
| Propylene glycol | 2.0 | Solubilizer |
| Methylparaben | 0.18 | Preservative |
| Propylparaben | 0.02 | Preservative |
| Butylated hydroxyanisole (BHA) | 0.02 | Antioxidant |
| Sodium citrate dihydrate | 0.45 | Buffering agent |
| Citric acid | 0.29 | Buffering agent |
| Anise oil | 1.0 | Flavoring agent |
| Cherry oil | 1.0 | Flavoring agent |
| Sucrose | 1.0 | Sweetening agent |
| Saccharin sodium dihydrate | 1.0 | Sweetening agent |
| Purified water QS AD | 48.8 | Solvent |

Example 5

| Constituent | Amount (% w/w) | Function |
|---|---|---|
| Ezetimibe | 0.2 | API |
| Simvastatin | 1.6 | API |
| Polyoxyethylene glycol 35 castor oil | 21.2 | Stabilizer/Solubilizer |
| Labrasol | 21.2 | Stabilizer/Solubilizer |
| Propylene glycol | 2.0 | Solubilizer |
| Methylparaben | 0.18 | Preservative |
| Propylparaben | 0.02 | Preservative |
| Butylated | 0.02 | Antioxidant |

-continued

| Constituent | Amount (% w/w) | Function |
|---|---|---|
| hydroxyanisole (BHA) | | |
| Sodium citrate dihydrate | 0.45 | Buffering agent |
| Citric acid | 0.29 | Buffering agent |
| Anise oil | 1.0 | Flavoring agent |
| Cherry oil | 1.0 | Flavoring agent |
| Sucrose | 1.0 | Sweetening agent |
| Saccharin sodium dihydrate | 1.0 | Sweetening agent |
| Purified water QS AD | 48.8 | Solvent |

Example 6

| Constituent | Amount (% w/w) | Function |
|---|---|---|
| Amlodipine | 0.1 | API |
| Simvastatin | 0.8 | API |
| Labrasol | 22.5 | Stabilizer/Solubilizer |
| Polyoxyethylene glycol 35 castor oil | 22.5 | Stabilizer/Solubilizer |
| Propylene glycol | 2.0 | Solubilizer |
| Dehydrated Ethanol | 2.6 | Solubilizer |
| Methylparaben | 0.18 | Preservative |
| Propylparaben | 0.02 | Preservative |
| Butylated hydroxyanisole (BHA) | 0.02 | Antioxidant |
| Sodium citrate dihydrate | 0.45 | Buffering agent |
| Citric acid | 0.29 | Buffering agent |
| Anise oil | 1.0 | Flavoring agent |
| Cherry oil | 1.0 | Flavoring agent |
| Sucrose | 1.0 | Sweetening agent |
| Saccharin sodium dihydrate | 1.0 | Sweetening agent |
| Purified water QS AD | 44.5 | Solvent |

Example 7

| Constituent | Amount (% w/w) | Function |
|---|---|---|
| Amlodipine | 0.1 | API |
| Fenofibrate | 1.6 | API |
| Labrasol | 22.5 | Stabilizer/Solubilizer |
| Polyoxyethylene glycol 35 castor oil | 22.5 | Stabilizer/Solubilizer |
| Propylene glycol | 2.0 | Solubilizer |
| Dehydrated Ethanol | 2.6 | Solubilizer |
| Methylparaben | 0.18 | Preservative |
| Propylparaben | 0.02 | Preservative |
| Butylated hydroxyanisole (BHA) | 0.02 | Antioxidant |
| Sodium citrate dihydrate | 0.45 | Buffering agent |
| Citric acid | 0.29 | Buffering agent |
| Anise oil | 1.0 | Flavoring agent |
| Cherry oil | 1.0 | Flavoring agent |
| Sucrose | 1.0 | Sweetening agent |
| Saccharin sodium dihydrate | 1.0 | Sweetening agent |
| Purified water QS AD | 43.7 | Solvent |

Example 8

| Constituent | Amount (% w/w) | Function |
|---|---|---|
| Amlodipine | 0.1 | API |
| Atorvastatin | 0.8 | API |
| Labrasol | 22.5 | Stabilizer/Solubilizer |
| Polyoxyethylene glycol 35 castor oil | 22.5 | Stabilizer/Solubilizer |
| Propylene glycol | 2.0 | Solubilizer |
| Dehydrated Ethanol | 2.6 | Solubilizer |
| Methylparaben | 0.18 | Preservative |
| Propylparaben | 0.02 | Preservative |
| Butylated hydroxyanisole (BHA) | 0.02 | Antioxidant |
| Sodium citrate dihydrate | 0.45 | Buffering agent |
| Citric acid | 0.29 | Buffering agent |
| Anise oil | 1.0 | Flavoring agent |
| Cherry oil | 1.0 | Flavoring agent |
| Sucrose | 1.0 | Sweetening agent |
| Saccharin sodium dihydrate | 1.0 | Sweetening agent |
| Purified water QS AD | 44.5 | Solvent |

Example 9

| Constituent | Amount (% w/w) | Function |
|---|---|---|
| Fenofibrate | 1.6 | API |
| Labrasol | 22.5 | Stabilizer/Solubilizer |
| Polyoxyethylene glycol 35 castor oil | 22.5 | Stabilizer/Solubilizer |
| Propylene glycol | 2.0 | Solubilizer |
| Dehydrated Ethanol | 2.6 | Solubilizer |
| Methylparaben | 0.18 | Preservative |
| Propylparaben | 0.02 | Preservative |
| Butylated hydroxyanisole (BHA) | 0.02 | Antioxidant |
| Sodium citrate dihydrate | 0.45 | Buffering agent |
| Citric acid | 0.29 | Buffering agent |
| Anise oil | 1.0 | Flavoring agent |
| Cherry oil | 1.0 | Flavoring agent |
| Sucrose | 1.0 | Sweetening agent |
| Saccharin sodium dihydrate | 1.0 | Sweetening agent |
| Purified water QS AD | 43.8 | Solvent |

Example 10

| Constituent | Amount (% w/w) | Function |
|---|---|---|
| Atorvastatin | 1.6 | API |
| Fenofibrate | 1.6 | API |
| Labrasol | 22.5 | Stabilizer/Solubilizer |
| Polyoxyethylene glycol 35 castor oil | 22.5 | Stabilizer/Solubilizer |
| Propylene glycol | 2.0 | Solubilizer |
| Dehydrated Ethanol | 2.6 | Solubilizer |
| Methylparaben | 0.18 | Preservative |
| Propylparaben | 0.02 | Preservative |
| Butylated hydroxyanisole (BHA) | 0.02 | Antioxidant |
| Sodium citrate dihydrate | 0.45 | Buffering agent |
| Citric acid | 0.29 | Buffering agent |
| Anise oil | 1.0 | Flavoring agent |
| Cherry oil | 1.0 | Flavoring agent |
| Sucrose | 1.0 | Sweetening agent |

-continued

| Constituent | Amount (% w/w) | Function |
|---|---|---|
| Saccharin sodium dihydrate | 1.0 | Sweetening agent |
| Purified water QS AD | 42.0 | Solvent |

Example 11—Stability Study of Oral Formulations of Ezetimibe and Simvastatin at Ambient Temperature The liquid formulations were stored in sealed 4 ounce clear glass bottles at ambient room temperature; and at appropriate time intervals, samples were withdrawn and subjected to HPLC analysis, pH measurement, and physical observation. The stability summary data is provided in Table 1 below:

TABLE 1

Stability Data After Storage at Ambient Temperature Condition (23-25° C.)

| | Prototype Formulation of Example 2 | | | |
|---|---|---|---|---|
| Test | Initial | 7 day | 22 day | 30 day |
| Appearance | CPC* | CPC | CPC | CPC |
| pH | 4.6 | 4.5 | 4.5 | 4.6 |
| Ezetimibe Assay (mg/mL) | 100% of initial assay | 100% | 103.5% | 101% |
| Simvastatin Assay (mg/mL) | 100% of initial assay | 99.8% | 99.5% | 99.4% |

*CPC denotes clear pink color with no visible particles

The Following Methods were Used to Evaluate the Formulation

HPLC Assay Method for Ezetimibe and Simvastatin

The HPLC column is Phenomenex Luna C18(2), 5 um, 4.6 mm×250 mm. The mobile phases consist of mobile phase A (MP-A): deionized water/methanol 2:1 (v/v), and mobile B: acetonitrile (MP-B). The following mobile phase (MP) flow program was used: 0-7 min, 55% of MP-A; 7-8 min, 55% to 30% of MP-A; 8-21 min, 30% of MP-A; 21-21.5 min, 30-55% of MP-A. The flow rate is 1 mL/min and column temperature was set at 35° C.

pH Measurement and Physical Observation

The pH meter was calibrated with pH 4.00 and pH 7.00 standards to give a slope of >97%. The pH of the oral liquid formulations was measured after calibration. The oral liquid formulations were observed under room light against a white/black background.

In addition, the dispersibility of the liquid formulation of Example 2 in purified water and its droplet size and zeta potential were also measured, which revealed that the formulation is easily redispersible in water and that the mean droplet size is 99.2+/−3.8 nm and zeta potential is −12.2+/−1.4 mV.

The following method can be used to evaluate the oral formulations comprising atorvastatin, fenofibrate and amlodipine The HPLC column is Phenomenex Luna C18(2), 5 um, 4.6 mm×250 mm. The mobile phases consist of mobile phase A (MP-A): 0.2% v/v phosphoric acid, pH adjusted to 4.0 with 1M NaOH; and mobile B: acetonitrile/methanol 1:1 (v/v) (MP-B). The following mobile phase (MP) flow program was used: 0-7 min, 47% of MP-A; 7-11 min, 47% to 20% of MP-A; 11-22 min, 20% of MP-A; 22-22.5 min, 20-47% of MP-A. The flow rate and column temperature were set at 1 mL/min and 35° C., respectively.

The invention illustratively described herein suitably may be practiced in the absence of any element or elements, limitation or limitations which is not specifically disclosed herein. Thus, for example, in each instance herein, any of the terms "comprising," "consisting essentially of" and "consisting of" may be replaced with either of the other two terms. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. An oral liquid formulation, comprising: (a) a combination of drugs wherein the drugs are selected from the group consisting of ezetimibe, statins, fenofibrate, amlodipine, valsartan, candesartan, telmisartan, losartan and salts thereof; (b) about 20% to about 90% w/w of one or more non-ionic surfactants that are liquids at ambient conditions; (c) about 0.05% to about 7.5% w/w of a co-solvent selected from the group consisting of an oil, glycerin, propylene glycol, polyethylene glycols that are liquids at ambient conditions, C1-C6 straight and branch monoalcohols and combinations thereof; (d) about 0.1% to about 5% w/w of a buffering agent, and (e) water wherein if present the ezetimibe is present in an amount of 0.05% to 10% w/w and if present the statins, fenofibrate, amlodipine, valsartan, candesartan, telmisartan, losartan and salts thereof are present in an amount of 0.05% to 20% w/w.

2. The oral liquid formulation of claim 1, wherein the combination of drugs are selected from the group consisting of: (i) a combination of ezetimibe and a statin or salt thereof; (ii) a combination of ezetimibe and fenofibrate or salt thereof; (iii) a combination of ezetimibe and amlodipine or salt thereof; (iv) a combination of a statin or salt thereof and fenofibrate or salt thereof; (v) a combination of a statin or salt thereof and amlodipine or salt thereof; and (vii) a combination of fenofibrate or salt thereof and amlodipine or salt thereof.

3. The oral liquid formulation of claim 1 further comprising one or more excipients selected from an antioxidant, a preservative, an antimicrobial, a pH adjusting agent, a sweetening agent, a flavoring agent, a viscosity enhancing agent, a hydrophilic stabilizing agent and combinations thereof.

4. The oral liquid formulation of claim 3, wherein the preservative is selected from the group consisting of methyl parahydroxybenzoate, ethylparahydroxybenzoate, propylparahydroxybenzoate, sorbic acid, potassium sorbate, and combinations thereof; the antioxidant is selected from the group consisting of butylated hydroxyanisole, butylated hydroxytoluene, ascorbic acid, and combinations thereof; the buffering agent is selected from the group consisting of citric acid, acetic acid, ascorbic acid, sodium citrate, sodium acetate, sodium ascorbate, disodium hydrogen phosphate, and combinations thereof; the sweetening agent is selected from the group consisting of sucrose, sorbitol, sodium saccharin, acesulfame potassium, xylitol, fructose, sucralose, and combinations thereof; and the flavoring agent is selected from the group consisting of citric acid, mint, spearmint, peppermint, wintergreen, anise, walnut, almond, menthol, lemon, lime, orange, grape, cherry, raspberry, bubblegum, chocolate extracts or oils, vanilla extracts or oils and combinations thereof.

5. The oral liquid formulation of claim 3, comprising: 0.05% to 10% w/w of ezetimibe, polyoxyethylene 35 castor oil, caprylocaproyl polyoxylglycerides, one or more antioxidants, one or more preservatives, sodium citrate, citric acid, sucrose, and saccharin sodium.

6. The oral liquid formulation of claim 3, comprising: 0.05% to 10% w/w of fenofibrate or salt thereof, polyoxyethylene 35 castor oil, caprylocaproyl polyoxylglycerides, one or more antioxidants, one or more preservatives, sodium citrate, citric acid, sucrose, and saccharin sodium.

7. The oral liquid formulation of claim 3, comprising: 0.05% to 10% w/w of atorvastatin or salt thereof, polyoxyethylene 35 castor oil, caprylocaproyl polyoxylglycerides, one or more antioxidants, one or more preservatives, sodium citrate, citric acid, sucrose, and saccharin sodium.

8. The oral liquid formulation of claim 3, comprising: 0.05% to 10% w/w of simvastatin, polyoxyethylene 35 castor oil, caprylocaproyl polyoxylglycerides, one or more antioxidants, one or more preservatives, sodium citrate, citric acid, sucrose, and saccharin sodium.

9. The oral liquid formulation of claim 3, comprising: 0.05% to 10% w/w of ezetimibe, 0.05% to 10% w/w of simvastatin, caprylocaproyl polyoxylglycerides, one or more antioxidants, one or more preservatives, sodium citrate, citric acid, sucrose, and saccharin sodium.

10. The oral liquid formulation of claim 3, comprising: 0.05% to 10% w/w of ezetimibe, 0.05% to 10% w/w of atorvastatin or salt thereof, caprylocaproyl polyoxylglycerides, one or more antioxidants, one or more preservatives, sodium citrate, citric acid, sucrose, and saccharin sodium.

11. The oral liquid formulation of claim 3, comprising: 0.05% to 10% w/w of ezetimibe, 0.05% to 10% w/w of fenofibrate or salt thereof, caprylocaproyl polyoxylglycerides, one or more antioxidants, one or more preservatives, sodium citrate, citric acid, sucrose, and saccharin sodium.

12. The oral liquid formulation of claim 3, comprising 0.05% to 10% w/w of fenofibrate or salt thereof, 0.05% to 10% w/w of simvastatin, caprylocaproyl polyoxylglycerides, one or more antioxidants, one or more preservatives, sodium citrate, citric acid, sucrose, and saccharin sodium.

13. The oral liquid formulation of claim 3, comprising: 0.05% to 10% w/w of fenofibrate or salt thereof, 0.05% to 10% w/w of atorvastatin or salt thereof, polyoxyethylene 35 castor oil, caprylocaproyl polyoxylglycerides, one or more antioxidants, one or more preservatives, sodium citrate, citric acid, sucrose, and saccharin sodium.

14. The oral liquid formulation of claim 3, comprising: 0.05% to 10% w/w of amlodipine or salt thereof, polyoxyethylene 35 castor oil, caprylocaproyl polyoxylglycerides, one or more antioxidants, one or more preservatives, sodium citrate, citric acid, sucrose, and saccharin sodium.

15. The oral liquid formulation of claim 3, comprising: 0.05% to 10% w/w of ezetimibe, 0.05% to 10% w/w of amlodipine or salt thereof, polyoxyethylene 35 castor oil, caprylocaproyl polyoxylglycerides, one or more antioxidants, one or more preservatives, sodium citrate, citric acid, sucrose, and saccharin sodium.

16. The oral liquid formulation of claim 3, comprising: 0.05% to 10% w/w of atorvastatin or salt thereof, 0.05% to 10% w/w of amlodipine or salt thereof, polyoxyethylene 35 castor oil, caprylocaproyl polyoxylglycerides, one or more antioxidants, one or more preservatives, sodium citrate, citric acid, sucrose, and saccharin sodium.

17. The oral liquid formulation of claim 3, comprising: 0.05% to 10% w/w of simvastatin, 0.05% to 10% w/w of amlodipine or salt thereof, polyoxyethylene 35 castor oil, caprylocaproyl polyoxylglycerides, one or more antioxidants, one or more preservatives, sodium citrate, citric acid, sucrose, and saccharin sodium.

18. The oral liquid formulation of claim 3, comprising: 0.05% to 10% w/w of fenofibrate or salt thereof, 0.05% to 10% w/w of amlodipine or salt thereof, polyoxyethylene 35 castor oil, caprylocaproyl polyoxylglycerides, one or more antioxidants, one or more preservatives, sodium citrate, citric acid, sucrose, and saccharin sodium.

19. A method of treating hyperlipidemia, mixed dyslipidemia, heterozygous familial hypercholesterolemia, atherosclerotic cardiovascular disease, hypertension, or coronary artery disease, comprising administering to a patient in need thereof a therapeutically effective amount of an oral liquid formulation according to claim 1.

20. The oral liquid formulation of claim 1 wherein the one or more non-ionic surfactants that are liquids at ambient conditions comprises a combination of (i) one or more non-ionic surfactants with an HLB value of 10 or greater and (ii) one or more non-ionic surfactants with an HLB value of less than 10 and the weight ratio of (i) to (ii) is 0.2:1 to 1:0.2.

21. The oral liquid formulation of claim 1 wherein the one or more non-ionic surfactants that are liquids at ambient conditions comprises a combination of (i) one or more non-ionic surfactants with an HLB value of 10 or greater and (ii) one or more non-ionic surfactants with an HLB value of less than 10 and the weight ratio of (i) to (ii) is 0.5:1 to 1:0.5.

22. The oral liquid formulation of claim 1 wherein the co-solvent is present in an amount of about 0.5% to about 5% w/w.

* * * * *